United States Patent [19]

Shiber

[11] Patent Number: 4,842,579
[45] Date of Patent: Jun. 27, 1989

[54] ATHERECTOMY DEVICE

[75] Inventor: Samuel Shiber, Mundelein, Ill.

[73] Assignee: Surgical Systems & Instruments, Inc., Mundelein, Ill.

[21] Appl. No.: 225,880

[22] Filed: Jul. 29, 1988

Related U.S. Application Data

[63] Continuation-in-part of Ser. No. 018,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^4$ .............................................. A61B 17/32
[52] U.S. Cl. ....................................... 604/22; 128/305
[58] Field of Search ............... 128/305, 753, 754, 311; 604/22

[56] References Cited

U.S. PATENT DOCUMENTS

| | | | |
|---|---|---|---|
| 1,123,730 | 1/1915 | Greenfield | 128/310 |
| 1,596,754 | 8/1926 | Moschelle | 604/282 |
| 2,505,358 | 4/1950 | Gusberg et al. | 128/751 |
| 2,955,591 | 10/1960 | MacLean | 128/756 |
| 3,614,953 | 10/1971 | Moss | 128/305.1 |
| 3,837,345 | 9/1974 | Matar | 129/305 |
| 4,020,847 | 5/1977 | Clark | 128/751 X |
| 4,030,503 | 6/1977 | Clark | 128/356 X |
| 4,177,797 | 12/1979 | Baylis et al. | 128/754 |
| 4,207,874 | 6/1980 | Choy | 128/303.1 X |
| 4,249,541 | 2/1981 | Pratt | 128/753 |
| 4,273,128 | 6/1981 | Lary | 128/305 |
| 4,306,570 | 12/1981 | Matthews | 128/310 X |
| 4,445,509 | 5/1984 | Auth | 128/305 |
| 4,479,497 | 10/1984 | Fogarty et al. | 128/344 |
| 4,589,412 | 5/1986 | Kensey | 128/305 |
| 4,627,436 | 12/1986 | Leckrone | 128/303.1 |
| 4,672,962 | 6/1987 | Hershenson | 128/303.1 |

FOREIGN PATENT DOCUMENTS

| | | | |
|---|---|---|---|
| 163502 | 12/1985 | European Pat. Off. | 128/328 |
| 2804015 | 8/1979 | Fed. Rep. of Germany | 128/305 |
| 665908 | 6/1979 | U.S.S.R. | 128/304 |
| 2044103 | 10/1980 | United Kingdom | 128/754 |

*Primary Examiner*—Michael H. Thaler
*Attorney, Agent, or Firm*—Samuel Shiber

[57] ABSTRACT

An atherectomy system for cutting, ingesting and removing an obstruction from within a patient's artery, having a flexible guide-wire insertable into the artery, a flexible rotary catheter being rotatably disposed and insertable into the artery over the flexible guide-wire, a blade at a distal end of the flexible rotary catheter having teeth on its periphery which are rounded and bent toward the center of the blade to ease insertion through the arteries and to reduce the probability of cutting the arterial wall during the insertion and cutting operation the blade having an outer wall which slidingly and rotatably bears against the arterial wall spreading the contact force on a relatively large area to minimize damage to the artery, a continuous passage defined between the rotating flexible rotary catheter and the flexible guide-wire, for ingesting the cut obstruction material.

5 Claims, 1 Drawing Sheet

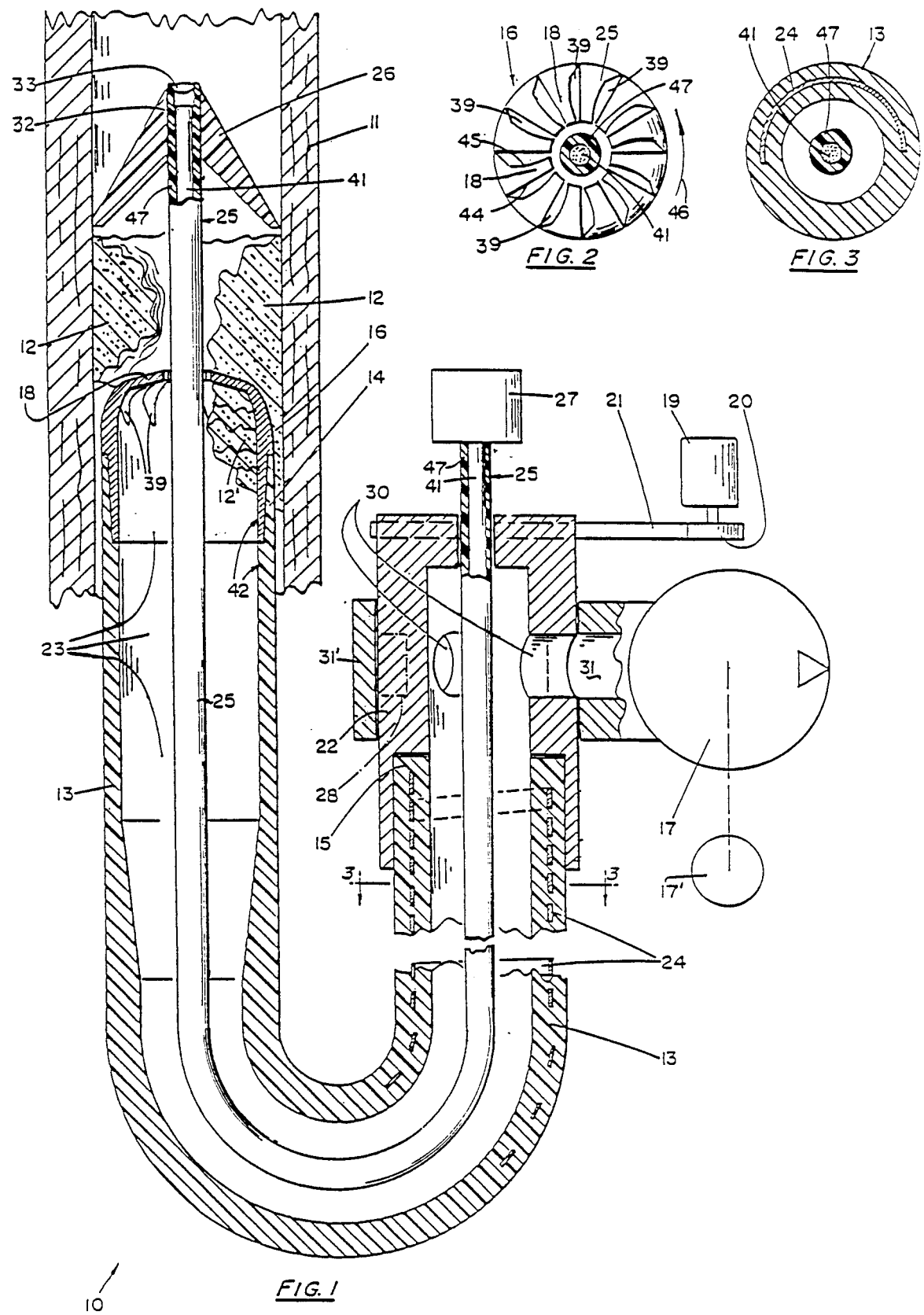

ATHERECTOMY DEVICE

CROSS REFERENCE TO OTHER APPLICATIONS

This application is a continuation in part of application Ser. No. 07/018,083 which was filed on Feb. 24, 1987, which is a continuation in part of application Ser. No. 06/874,546 which was filed on June 16, 1986 (now U.S. Pat. No. 4,732,154) which is a continuation in part of application Ser. No. 06/609,846 which was filed on May 14, 1984 (now abandoned). All the above prior applications are hereby being incorporated by reference.

BACKGROUND AND OBJECTIVES OF THE INVENTION

With age a large percentage of the population develops arterial obstructions formed by fats, fibrous material and calcified deposits, resulting in a diminished blood circulation. The disturbance to blood flow which these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Problems with this treatment are that it injures the arterial wall creating a rough lumen and in certain cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy catheter rotatable over a flexible guide-wire, equipped with a rotary cutting means at its distal end, that would cut and extract the obstruction material, including blood clots if present, create a smooth lumen and not crack the arterial wall. The design of an atherectomy catheter should lend itself to be produceable in diameters down to around 1 /mm (millimeter) and a length of up to a meter to be able to reach and enter small and remote arteries. Preferably, the operation of the atherectomy system would resemble the operation of present catheter systems, so that existing skills of the medical staff can be utilized. These and other objectives of the invention will become apparent from the following discussion and the accompanying drawings.

BRIEF DESCRIPTION OF THE FIGURES

FIG. 1 generally shows a cross sectional view of an atherectomy system according to the present invention.

FIG. 2 shows a distal end of the atherectomy system.

FIG. 3 shows a cross sectional view of the atherectomy system along a line 3—3 marked on FIG. 1.

DETAILED DESCRIPTION OF THE DRAWINGS

FIG. 1 shows the atherectomy system 10 for cutting, ingesting and removing an obstruction 12 from within a patient's vessel, an artery 11. As shown in FIG. 1, the atherectomy system comprises several elongated parts in a nested relationship, and their ends shall be referred to as "distal", meaning the end which goes into the artery and "proximal", meaning the other end. In view of the above, "distal direction" or the term "distally" shall indicate a general direction from the proximal end to the distal end, and "proximal direction" or "proximally" shall refer to an opposite direction.

The atherectomy system comprises:

A flexible guide-wire 25 which is insertable into the artery. Optionally, the flexible guide-wire is equipped with a distal barrier means in the form of a flexible collapsible umbrella 26 to counter distal movement of surrounding obstruction material while the blade cuts the obstruction material. The flexible guide-wire may also contain an optical fiber bundle 41 in a plastic jacket 47 and a lens 33 at its distal tip. An imaging unit and/or laser gun 27 may be optically coupled to the proximal end of the optical fiber bundle for analyzing the inside of the artery and/or opening, respectively, a pilot passage for the distal tip of the flexible guide-wire to pass through in a case of complete arterial blockage.

A flexible rotary catheter 13 is rotatably disposed and insertable into the artery, over the flexible guide-wire.

A stainless steel hollow blade 16 is attached to the distal end of the flexible rotary catheter. The blade has teeth 18 on its periphery which are rounded and bent toward the center of the blade to ease insertion through the arteries and to reduce the chance of cutting the wall of the artery during the insertion and cutting operation. A front edge 44 of the teeth is sharpened to cut the obstruction material to pieces 12' which pass into a continuous passage 23 through spaces 39 between the teeth while the blade rotates forward in a direction of arrow 46 (note FIG. 2). A back side 45 of the teeth is dull to allow a backwards rotation while manipulating and advancing the flexible rotary catheter through the arterial system towards the obstruction with a reduced risk of injuring the arterial wall. The blade has an outer wall 16' which slidingly and rotatably bears against the artery spreading the contact force on a relatively large area and thereby minimizing the damage to the artery. A rotating inner-wall 42 is formed by the inside surfaces of the blade and of the flexible rotary catheter.

The continuous passage 23 is defined between the rotating inner-wall and the flexible guide-wire, and the relative motion between the inner-wall and the flexible guide-wire mechanically acts on the ingested obstruction material in the continuous passage and enables it to move towards the proximal end 15 of the flexible rotary catheter and make room for an additional cut material.

Coupling means affixed to the proximal end of the flexible rotary catheter in the form of a hub 22 is frictionally engaged with a flat belt 21 which couples the flexible rotary catheter to a rotating means in the form of a motor 19 having a pulley 20. The proximal end of the flexible guide-wire slidingly and rotatably extends through the hub.

Suction can be applied to the proximal end of the flexible rotary catheter by a suction pump 17 driven by a motor 17', through ports 30 which alternately communicate with a port 31 formed in a sleeve 31', as the hub rotates in the sleeve 31'. Alternatively, a groove 28 (shown in phantom lines) can provide continuous communication between the continuous passage 23 and the port 31. The suction cooperates with the mechanical action taking place in the continuous passage in proximally moving the cut obstruction material 12'.

Torque generated by the motor is partially dissipated by frictional losses along the flexible rotary catheter, therefore, the flexible rotary catheter can be manufactured with an increased wall thickness and increased torque carrying capacity at the vicinity of its proximal end compared with the same at its distal end (note FIG. 1), and the wall can be reinforced by a spiral ribbon made from metal 24 (note FIGS. 1 and 3). The atherectomy system can be manufactured in different diameters and lengths depending on the size and site of artery that it is intended for and on whether the system is to be used percutaneously (that is through the skin) or intra-operatively (that is when the artery is surgically exposed for inserting the system into the artery).

A process for removing an obstruction from a artery with an atherectomy system, comprises the following steps:

Conventionally inserting into a artery, into an obstruction, a flexible guide-wire.

Advancing over the flexible guide-wire a blade 16 located at a distal end of an atherectomy catheter.

Advancing the blade to the obstruction and cutting the obstruction. During the operation the flexible guide-wire and the flexible introducer sleeve (if present) are prevented from being rotationally dragged by the blade. Fluid can be delivered to the obstruction site through the flexible sleeve, around the atherectomy catheter. Such fluid can lubricate and cool the cutting process and provide a medium for flushing particles of obstruction material into the atherectomy catheter, especially in conjunction with suction applied to the proximal end of the atherectomy catheter. The fluid may be radio-opaque to assist x-raying the process. Prior to cutting, fluid can also be delivered through the atherectomy catheter. A mechanical action between the blade, the flexible rotary catheter and the flexible guide-wire on the cut obstruction material due to the relative motion between them enables the cut material into the continuous passage defined in the atherectomy catheter and around the flexible guide-wire.

Removing the catheter containing the obstruction material out of the artery.

The sequence of insertion of the components into the artery may vary depending on the nature and the location of the obstruction and the preferences of the medical staff. Additional steps may be added to assist the process. For example, a standard guiding catheter, which is either straight or pre-bent, may be inserted into the artery to assist in placing the flexible-guide-wire and the atherectomy catheter in the obstruction site.

When an arterial obstruction is further blocked by a fresh blood clot, as is often the case in a heart attack, the flexible guide-wire can usually be inserted through the fresh clot and the atherectomy system, preferably while employing suction, can be used to clear the clot in order to restore blood passage through the artery and alleviate the acute heart attack. Then the system can be utilized to cut the underlying atherosclorotic obstruction providing a long term correction to the condition that induced the attack.

While the present invention has been illustrated by a single embodiment, it should be understood that various modifications and substitutions may be made without departing from the spirit of the invention or the scope of the claims.

I claim:

1. An atherectomy system for cutting, ingesting and removing an obstruction from within a patient's artery, comprising in combination:
    a flexible guide-wire insertable into the artery,
    a flexible rotary catheter being rotatably disposed and insertable into the artery, over said flexible guide-wire,
    a blade at a distal end of said flexible rotary catheter for cutting an obstruction located in front of said blade, said blade having teeth on its periphery which are rounded and bent toward the center of the blade and an outer wall for slidingly and rotatably bearing against the artery,
    a rotating inner-wall formed by the inside surfaces of said flexible rotary catheter and said blade,
    a continuous passage surrounding said flexible guide-wire for ingesting the cut obstruction material, said continuous passage being defined between said rotating inner-wall and said flexible guide-wire,
    coupling means at said proximal end of said flexible rotary catheter for coupling it to a rotating means.

2. An atherectomy system as in claim 1, wherein suction is applied at said proximal end of said continuous passage to proximally pull the cut obstruction material in said continuous passage.

3. An atherectomy system as in claim 1, said flexible guide-wire having distal barrier means to counter distal movement of surrounding obstruction material while said blade cuts the obstruction material.

4. An atherectomy system as in claim 1, said flexible guide-wire containing an optical fiber.

5. An atherectomy system as in claim 1, wherein said flexible rotary catheter has a higher torque carrying capacity in the vicinity of said proximal end than in the vicinity of said distal end.

* * * * *

REEXAMINATION CERTIFICATE (2711th)
United States Patent [19]

Shiber

[11] B1 4,842,579

[45] Certificate Issued Oct. 31, 1995

[54] ATHERECTOMY DEVICE

[75] Inventor: Samuel Shiber, Mundelein, Ill.

[73] Assignee: Surgical Systems & Instruments, Inc., Mundelein, Ill.

Reexamination Request:
No. 90/003,608, Oct. 19, 1994

Reexamination Certificate for:
Patent No.: 4,842,579
Issued: Jun. 27, 1989
Appl. No.: 225,880
Filed: Jul. 29, 1988

Related U.S. Application Data

[63] Continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^6$ .............................. A61B 17/22; A61B 17/32
[52] U.S. Cl. .............................................. 604/22; 606/159
[58] Field of Search ................................................ 606/159

[56] References Cited

U.S. PATENT DOCUMENTS

| | | |
|---|---|---|
| 4,464,176 | 8/1984 | Wijayarathna . |
| 4,690,140 | 9/1987 | Mecca ...................................... 606/159 |
| 4,696,667 | 9/1987 | Masch . |
| 4,784,636 | 11/1988 | Rydell . |
| 4,886,490 | 12/1989 | Shiber . |
| 4,887,613 | 12/1989 | Farr et al. . |
| 4,895,166 | 1/1990 | Farr et al. . |
| 4,926,858 | 5/1990 | Gifford et al. ........................ 606/159 |

OTHER PUBLICATIONS

Oesterle et al., "Independently Movable Guidewire Techniques for Percutaneous Coronary Angioplasty," *Angioplasty*, chapter 15, pp. 295–308 (1986, G. David Jang et al., eds., McGraw–Hill Book New York.

Simpson et al., "A New Catheter System for Coronary Angioplasy," *Am. J. Cardiol.*, pp. 12–16, 49, 1982.

Dervan et al., "Transluminal Angioplasty of Occluded Coronary Arteries, Use of a Movable Guide Wire System," *Circulation*, pp. 776–784, vol. 68 No. 4, 1983.

Hall, David and Andreas Gruentzig, "Percutaneous Transluminal Coronary Angioplasty," *Am. J. Roent.*, pp. 13–16, 142, 1984.

*Primary Examiner*—Michael H. Thaler

[57] ABSTRACT

An atherectomy system for cutting, ingesting and removing an obstruction from within a patient's artery, having a flexible guide-wire insertable into the artery, a flexible rotary catheter being rotatably disposed and insertable into the artery over the flexible guide-wire, a blade at a distal end of the flexible rotary catheter having teeth on its periphery which are rounded and bent toward the center of the blade to ease insertion through the arteries and to reduce the probability of cutting the arterial wall during the insertion and cutting operation the blade having an outer wall which slidingly and rotatably bears against the arterial wall spreading the contact force on a relatively large area to minimize damage to the artery, a continuous passage defined between the rotating flexible rotary catheter and the flexible guide-wire, for ingesting the cut obstruction material.

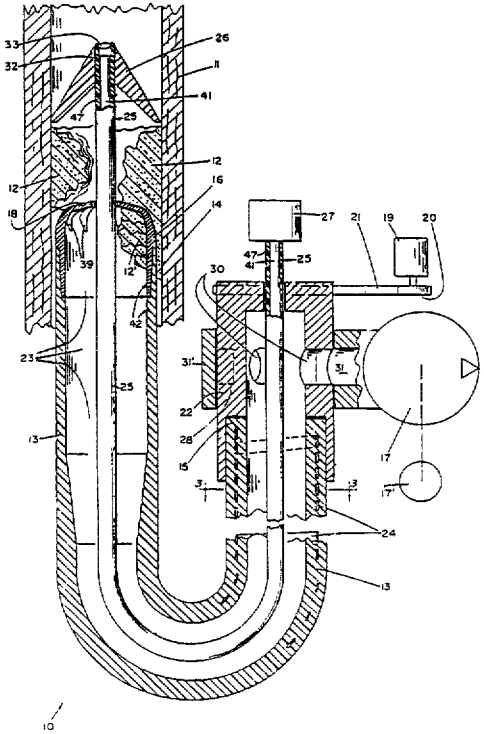

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1–5 is confirmed.

* * * * *